United States Patent [19]
Carr et al.

[11] Patent Number: 5,707,823
[45] Date of Patent: Jan. 13, 1998

[54] CONTAINERS

[75] Inventors: Anthony Hugh Carr; Judith Marjorie Anderson; Roy Holbrook, all of Bedford, Great Britain

[73] Assignee: Oxoid Limited, Hampshire, England

[21] Appl. No.: 505,266

[22] PCT Filed: Feb. 9, 1994

[86] PCT No.: PCT/GB94/00254

§ 371 Date: Dec. 12, 1995

§ 102(e) Date: Dec. 12, 1995

[87] PCT Pub. No.: WO94/19453

PCT Pub. Date: Sep. 1, 1994

[30] Foreign Application Priority Data

Feb. 17, 1993 [EP] European Pat. Off. ............ 93301170

[51] Int. Cl.$^6$ ................ C12Q 1/02; C12Q 1/00; B65D 39/12; B65D 53/00
[52] U.S. Cl. ............... 435/29; 435/4; 435/287; 435/808; 435/291; 435/296; 435/298; 435/299; 422/102; 422/82.13; 422/68.1; 215/271; 215/270; 215/274; 215/341
[58] Field of Search ............... 435/29, 4, 287.5, 435/288.1, 287, 808, 291, 296, 298, 299; 215/232, 270, 271, 274, 341; 422/68.1, 102, 82.13

[56] References Cited

U.S. PATENT DOCUMENTS

| | | | |
|---|---|---|---|
| 3,781,779 | 12/1973 | Tallman | 215/232 |
| 4,248,355 | 2/1981 | Kolb et al. | 215/274 |
| 4,547,900 | 10/1985 | Larkin et al. | 215/232 |
| 4,773,552 | 9/1988 | Boege et al. | 215/232 |
| 5,051,360 | 9/1991 | Waters | 435/34 |

FOREIGN PATENT DOCUMENTS 171926  2/1986  European Pat. Off. .

OTHER PUBLICATIONS

Webster's Dictionary, p. 131 and p. 305, 1984 Month Not Available.

*Primary Examiner*—Louise Leary
*Attorney, Agent, or Firm*—Cushman Darby & Cushman IP Group Pillsbury Madison & Sutro LLP

[57] ABSTRACT

A gas-tight container incorporates a flexible diaphragm made of chlor-butyl rubber. The container finds particular use in systems for monitoring growth of microorganisms.

12 Claims, 1 Drawing Sheet

CONTAINERS

FIELD OF THE INVENTION

This invention relates to containers and is concerned particularly, but not exclusively, with blood culture bottles.

BACKGROUND TO THE INVENTION

The specification of PCT/GB92/01327 (WO93/03178) concerns a method and apparatus for monitoring the growth of micro-organisms, for example in blood culture bottles. The specification describes and claims, inter alia, a method of monitoring the growth of micro-organisms in liquid culture in a gas-tight container incorporating a flexible diaphragm capable of moving in response to pressure changes within the container, by detecting displacement of the diaphragm, wherein the position or conformation of the diaphragm is repeatedly sensed using distance-measuring means.

Movement of the diaphragm is conveniently detected optically, typically by a laser.

The container is preferably constructed of rigid material, with the sole exception of the diaphram, so that the diaphragm alone is displaced in response to pressure changes within the container. The diaphragm is conveniently made of resilient flexible plastics or rubber material.

The container preferably comprises a culture bottle, having a bottle closure incorporating a resilient flexible plastics or rubber diaphragm (known as a septum) held in place by an annular aluminum overseal that is crimped under a lip extending around the bottle neck.

SUMMARY OF THE INVENTION

It has now been discovered that the diaphragm of such a container is with advantage made of chlor-butyl rubber.

In one aspect the invention thus provides a gas-tight container incorporating a flexible diaphragm, wherein the diaphragm comprises chlor-butyl rubber.

The properties of chlor-butyl rubber are found to be particularly well suited to the requirements of an optical monitoring system, eg as disclosed in PCT/GB92/01327 (WO93/03178).

Chlor-butyl rubber can be relatively light in colour and relatively non-absorbent at laser wavelengths which is an advantage for optical monitoring purposes, enabling greater sensitivity of detection than is possible with diaphragms of dark colour. For example, chlor-butyl rubber can be white, pink, red or blue at least. Blue is found to be a practical colour to use as it is compatible with laser monitoring and also cosmetically attractive (not contrasting too much with any blood left on the surface). Chlor-butyl rubber thus represents a significant improvement compared with alternative diaphragm materials such as butyl rubber, which is dark grey or black and which is relatively absorbent at laser lengths and so presents problems for optical monitoring.

Chlor-butyl rubber also has the necessary property of being substantially impermeable to gas, even over extended periods, so that a gaseous atmosphere can be maintained within the container even during prolonged storage. This is not possible with certain other materials, such as silicone rubber.

Chlor-butyl rubber is also able effectively to seal small punctures, eg. made when introducing a sample to be tested to the container via a needle passed through the diaphragm. A chlor-butyl rubber diaphragm can thus effectively seal needle "tracks" made when introducing samples, eg. blood samples, to the container.

Chlor-butyl rubber is also available in a range of hardness values (eg covering the range 40 to 50 Shore at least) that are well suited to the requirements of a pressure monitoring system, eg as disclosed in PCT/GB92/01327 (WO93/03178). Furthermore, because the hardness can be varied over a range of values it is possible to some extent to modify the sensitivity of the pressure responsiveness of the diaphragm by varying the hardness.

Furthermore, chlor-butyl rubber has the advantage of being mouldable, so that a chlor-butyl rubber diaphragm of any desired shape, configuration and thickness can be readily produced by a moulding process. A thickness in the range 2.7 to 3.2 mm is generally found to be suitable.

The container conveniently comprises a generally conventional culture bottle, typically made of glass. However, the bottle preferably has a larger opening than usual, to enable provision of as large an area of unsupported diaphram as possible to maximise response while still having a gas tight joint between the diaphragm and container. A 20 mm diameter circular opening is found to be an adequate compromise.

The diaphragm is conveniently held in place with an annular aluminum overseal crimped in position in generally conventional manner. However, the aluminum preferably has a matt or semi-matt finish, in place of the normally used reflective raw aluminum surface, and may for example have a semi-matt white lacquer finish. Provision of a matt or semi-matt finish is of advantage in a laser monitoring system, eg. as disclosed in PCT/GB92/01327 (WO93/03178), in which the overseal is scanned by the laser for reference purposes because the laser sensor cannot cope with the reflective surface of raw aluminum.

The container of the invention finds application particularly, but not exclusively, in methods and apparatus for monitoring the growth of micro-organisms in liquid culture as disclosed in PCT/GB92/01327 (WO93/03178).

In a further aspect, the invention thus provides a method of monitoring the growth of micro-organisms in liquid culture in a gas-tight container incorporating a flexible diaphragm of chlor-butyl rubber capable of moving in response to pressure changes within the container, by detecting displacement of the diaphragm, wherein the position or conformation of the diaphragm is repeatedly sensed using distance-measuring means.

The invention also provides apparatus for monitoring the growth of micro-organisms in liquid culture, comprising means for holding an array of gas-tight containers each containing a liquid test sample and each incorporating a flexible diaphragm of chlor-butyl rubber capable of moving in response to pressure changes within the container, distance-measuring means capable of detecting changes in position or conformation of each diaphragm, means for providing relative movement between the containers and the distance-measuring means for repeatedly presenting the containers individually in turn to the distance-measuring means, and means for recording and/or displaying data obtained from the distance-measuring means.

BRIEF DESCRIPTION OF DRAWINGS:

An embodiment of the invention will now be described, by way of illustration, with reference to the accompanying drawings, in which.

DETAILED DESCRIPTION OF THE DRAWINGS

Figure 1:
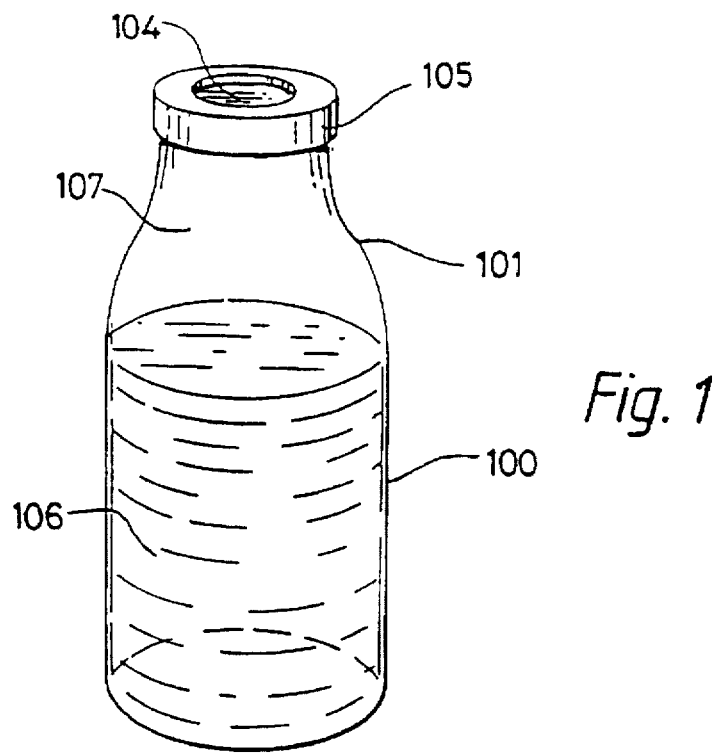
FIG. 1 is a perspective view of a blood culture bottle in accordance with the invention.
Figure 2:
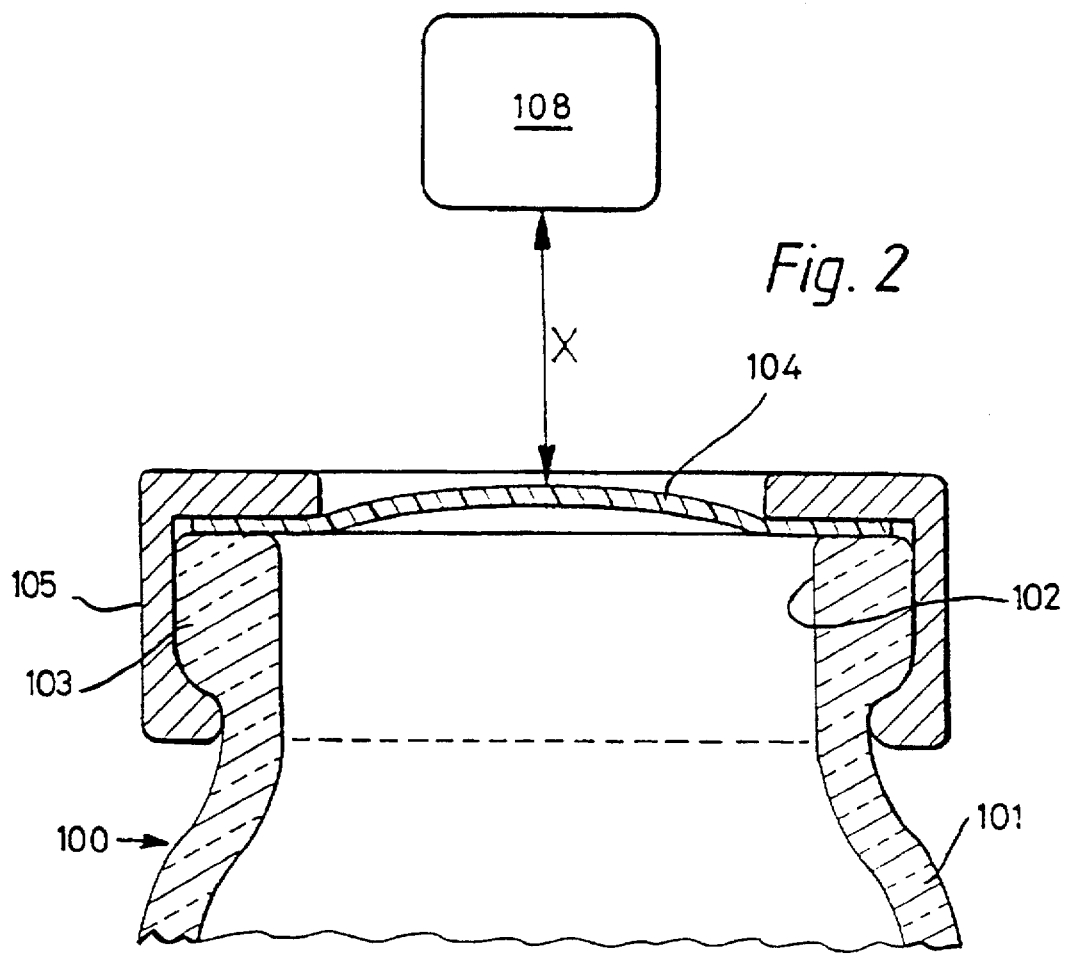
FIG. 2 is a vertical cross-section, to an enlarged scale, of the top part of the bottle shown in FIG. 1.

FIG. 1 shows a generally conventional culture bottle such as is widely used in laboratories and hospitals in the culturing of samples, such as blood samples, to detect the presence of micro-organisms. The culture bottle comprises a cylindrical glass bottle 100 of circular cross section with a gently tapering broad neck 101 terminating in a circular opening 102 surrounded by an enlarged external annular lip 103 (FIG. 2). Opening 102 is rather larger than is usual, having a diameter of 20 mm.

As best shown in FIG. 2, opening 102 is covered by a resilient, flexible septum or diaphragm 104 which, in accordance with the invention, is made of blue chlor-butyl rubber with a thickness of about 3.2 mm and a hardness of about 50 Shore. The diaphragm is sealed in place by an annular aluminum overseal 105 that is crimped in position under lip 103. The overseal 105 has a semi-matt white lacquer finish.

The bottles are normally supplied to the end user in sealed form containing an appropriate liquid growth medium 106 surmounted by a headspace 107. A sample, such as a sample of blood or other body fluid, can be injected directly into the culture bottle through the septum by use of a syringe, and the septum seals itself when the needle of the injecting syringe is withdrawn from the bottle.

Pressure variations within the sealed bottle can cause the septum or diaphragm 104 to deform inwardly or outwardly relative to the interior of the bottle, adopting a concave or convex configuration. Under normal circumstances there will always be a volume of gas in the head space 107 because the liquid growth medium 106 and injected sample will only occupy part of the bottle capacity. Changes in the internal pressure can result from temperature changes, eg warming of the bottle to normal culturing conditions. In general, culture is conducted at elevated temperature, eg. 37° C. If micro-organisms are present in the injected sample, they will grow in the medium and many species produce gas during growth. This also increases the internal pressure and causes the septum to deform outwardly further. Other species may cause a net reduction in the gas content of the bottle, and this leads to a drop in internal pressure and the septum deforms inwardly.

The bottles find particular use in an optical measuring system, eg. as disclosed in PCT/GB92/01327 (WO93/03178). Briefly, such a system relies on the measurement of small changes in the position or profile of the septum or diaphragm 104 relative to a fixed reference point, such as the rim of the crimped overseal 105. The centre of the septum 104 will rise and become convex, as shown in FIG. 2, if the pressure within the bottle increases. Alternatively the septum will drop and become concave if there is a reduction in internal pressure. By employing a laser 108 or similar sensitive distance-measuring device, which can scan repeatedly across the top of the bottle, the movement of the septum relative to the fixed position of the rim of the seal can be monitored.

The laser 108 measures distance X, between the laser and the centre of the septum, and also the distance between the laser and a fixed reference point on the bottle such as the rim of the seal to provide a measure of movement of the septum. Because the rim of the seal acts as a fixed reference point relative to the septum, the precise position of the bottle at the time of measurement does not matter.

The bottle can form part of an array of identical bottles with there being relative movement between the bottles and laser so that each bottle is scanned by the laser, eg. by moving the bottles in turn to a reading station associated with the laser, for example using a carousel arrangment, or by moving the laser over a fixed array of bottles. As noted above, there is no need for an individual bottle to be positioned in a precise relationship with the laser reader, because each bottle carries its own fixed internal reference (the rim of the seal). Therefore there are far fewer physical constraints on the design of the culturing/reading unit, and this offers considerable advantages over many commercially available multi-bottle culturing/recording systems.

See the specification of PCT/GB92/01327 (WO93/03178) for further details of the measuring system.

We claim:

1. A gas-tight container incorporating a flexible diaphragm wherein the diaphragm comprises blue chlorbutyl rubber.

2. A gas-tight container incorporating a flexible diaphragm wherein the diaphragm comprises chlorbutyl rubber which has a hardness in the range 40 to 50 Shore.

3. The container according to claim 1 or 2, wherein the diaphragm has a thickness in the range 2.7 to 3.2 mm.

4. The container according to claim 1 or 2, comprising a culture bottle.

5. The container according to claim 4, wherein the bottle has a circular opening 20 mm in diameter.

6. The container according to claim 1 or 2, wherein the diaphragm is sealed to the container with a crimped annular overseal.

7. The container according to claim 6, wherein the overseal has a matt or semi-matt finish.

8. The container according to claim 7, wherein the overseal is of aluminum and has a white semi-matt finish.

9. A method of monitoring the growth of micro-organisms in liquid culture in a gas-tight container incorporating a flexible diaphragm of chlor-butyl rubber capable of moving in response pressure changes within the container, by detecting displacement of the diaphragm, wherein the position or conformation of the diaphragm is repeatedly sensed using distance-measuring means.

10. Apparatus for monitoring the growth of micro-organisms in liquid culture, comprising of gas-tight container each containing a liquid test sample and incorporating a flexible diaphragm of chlor-butyl rubber capable of moving in response to pressure changes within the container and, distance-measuring means capable of detecting changes in position or conformation of said diaphragm.

11. A gas-tight container comprising a culture bottle incorporating a flexible diaphragm, wherein the diaphragm comprises chlor-butyl rubber.

12. A gas-tight container incorporating a flexible diaphragm, wherein the diaphragm comprises chlor-butyl rubber and the diaphragm is sealed to the container with a crimped annular overseal.

* * * * *